US00PP26172P3

(12) United States Plant Patent
Mazzardis

(10) Patent No.: US PP26,172 P3
(45) Date of Patent: Dec. 1, 2015

(54) BLUEBERRY PLANT, EB 8-21

(50) Latin Name: ***Vaccinium* Hybrid**
Varietal Denomination: EB 8-21

(71) Applicant: Vincent Mazzardis, Joondalup (AU)

(72) Inventor: Vincent Mazzardis, Joondalup (AU)

(73) Assignee: Prunus Persica Pty Ltd & Rolfe Nominees Pty Ltd (AU)

( * ) Notice: Subject to any disclaimer, the term of this patent is extended or adjusted under 35 U.S.C. 154(b) by 89 days.

(21) Appl. No.: 13/998,665

(22) Filed: Nov. 21, 2013

(65) Prior Publication Data

US 2014/0150141 P1 May 29, 2014

(30) Foreign Application Priority Data

Nov. 28, 2012 (AU) ..... 2012/257

(51) Int. Cl.
*A01H 5/00* (2006.01)
*A01H 5/08* (2006.01)

(52) U.S. Cl.
USPC ..... Plt./157
CPC ..... *A01H 5/08* (2013.01)

(58) Field of Classification Search
USPC ..... Plt./157
See application file for complete search history.

(56) References Cited

FOREIGN PATENT DOCUMENTS

AU 2012/257 11/2012

OTHER PUBLICATIONS

PLUTO Plant Variety Database Apr. 15, 2015. p. 1.*

* cited by examiner

*Primary Examiner* — Annette Para
(74) *Attorney, Agent, or Firm* — Randall Danskin PS

(57) ABSTRACT

A new and distinct variety of blueberry plant, which is denominated varietally as 'EB 8-21' and which produces fruit which are mature for harvesting and shipment early in the season, and which is very large in size and which further displays a growth pattern which is upright when grown under the ecological conditions prevailing in Yanchep Springs, Western Australia.

2 Drawing Sheets

Latin name: '*Vaccinium* Hybrid'.
Varietal denomination: 'EB 8-21'.

RELATED APPLICATION DATA

The present application claims priority to Australian Plan Breeders Rights Application Serial No. 2012/257 and which was filed on Nov. 28, 2012.

BACKGROUND OF THE NEW VARIETY

The present invention relates to a new, novel, and distinct variety of blueberry plant '*Vaccinium* Hybrid,' and which has been denominated varietally, as 'EB 8-21', hereinafter.

ORIGIN AND ASEXUAL REPRODUCTION OF THE NEW VARIETY

The present variety of blueberry plant resulted from an ongoing development program of plant breeding. The purpose of this program is to improve the commercial quality of various plant varieties by creating and releasing promising selections of plants including blueberries. To this end, I have made both controlled and hybrid cross-pollinations each year in order to produce experimental plant populations from which improved progenies are evaluated and selected.

The blueberry plant 'EB 8-21' was originated by me and selected from a population of new plants growing on my farm, and which is located near Yanchep Springs, Western Australia. The new plant was derived from a controlled pollination, which was conducted using the seed parent 'SB-1', and the pollen parent '03-6' during the 2005 growing season, on my farm which is located in Yanchep Springs, Yanchep Western Australia. The seed parent 'SB-1', and the pollen parent '03-6' are both unpatented. The seed parent is principally characterized as to novelty by a semi-spreading growth habit; an early season of flowering; and which further produces fruit having a medium size for the species. On the other hand, the pollen parent is characterized by a spreading growth habit; an early season of flowering; and which further produces large fruit. Seed derived from the seed parent ('SB-1') [unpatented], produced approximately 500 plants. The first fruit from this first cross-pollination was studied during the 2007 growing season.

A subsequent assessment took place in 2008, and the new variety 'EB 8-21' showed particularly desirable character traits. Further commercial testing including vegetative propagation from cuttings taken from 'EB 8-21' occurred during the 2009 through 2012 growing seasons. The resulting progeny appeared true to the original plant. Subsequent evaluations has led the inventor to conclude that the new variety is novel and distinct. The present variety is characterized as to novelty by producing extra large sized fruit, and which further has a small, dry picking scar, very good fruit flavor, and an early flowering and fruit production dates.

The closest known variety to the new variety 'EB 8-21' is the "Sharpeblue" blueberry plant (unpatented), and which produces fruit which are mature for harvesting and shipment early to the middle of the season, and which further has a fruit size which is average as compared to other blueberry plants. Still further, the "Sharpeblue" blueberry plant has an intermediate growth habit and a fruit shape which is considered to be oblate. The new plant 'EB 8-21', in contrast, has a date of fruit harvesting which is considered to be very early in the season, and which additionally produces very large fruit, and has an upright growth habit which is in contrast to the closest known variety.

BRIEF DESCRIPTION OF THE DRAWING

The accompanying drawings, which are provided are color photographs of the new blueberry plant.

FIG. 1 further depicts a twig bearing typical leaves and showing the dorsal and ventral coloration thereof, and the general growth habit of the new variety.

Figure 1:
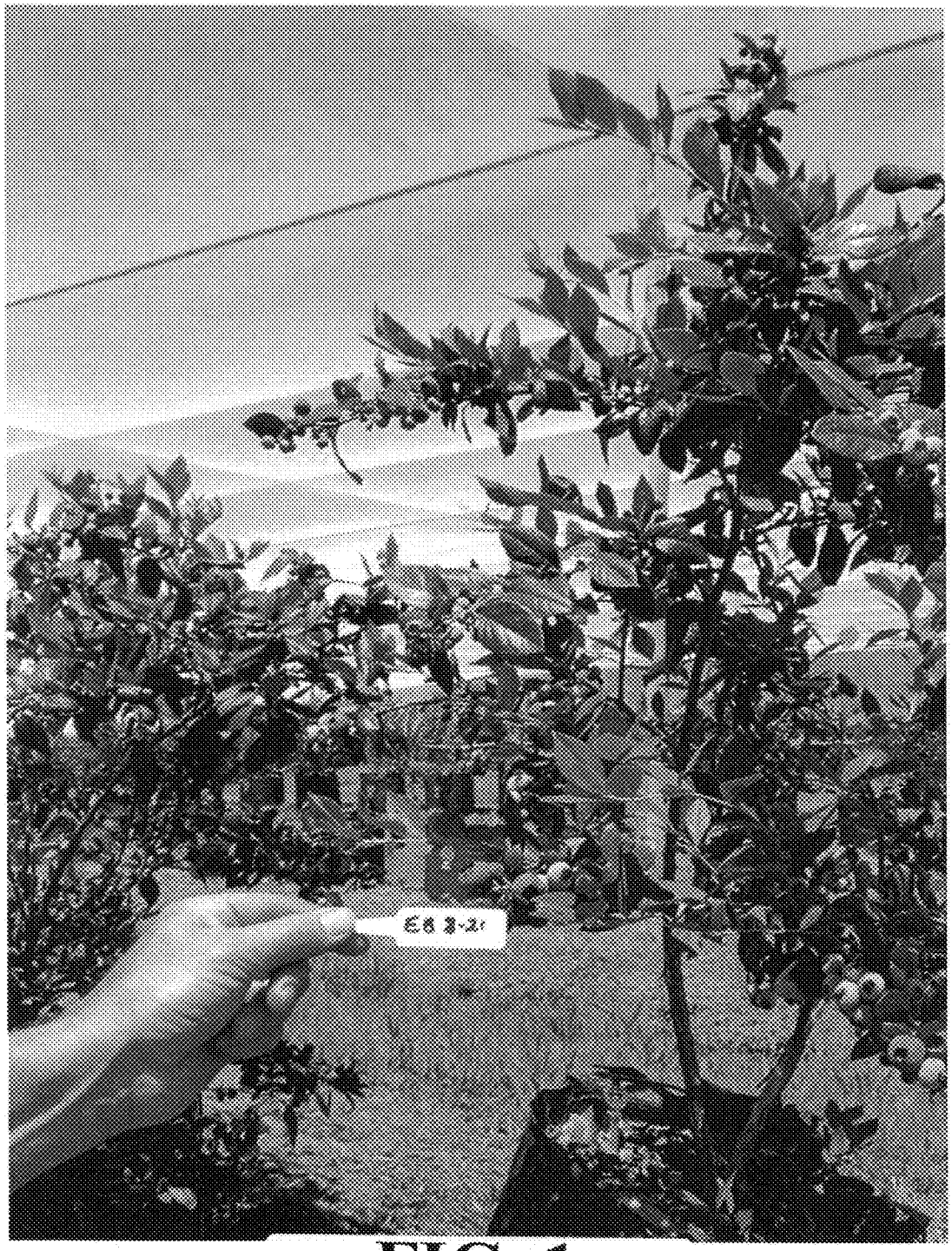
FIG. 1 depicts several whole, mature fruit of the new and novel variety, sufficiently matured for harvesting and shipment.
Figure 2:
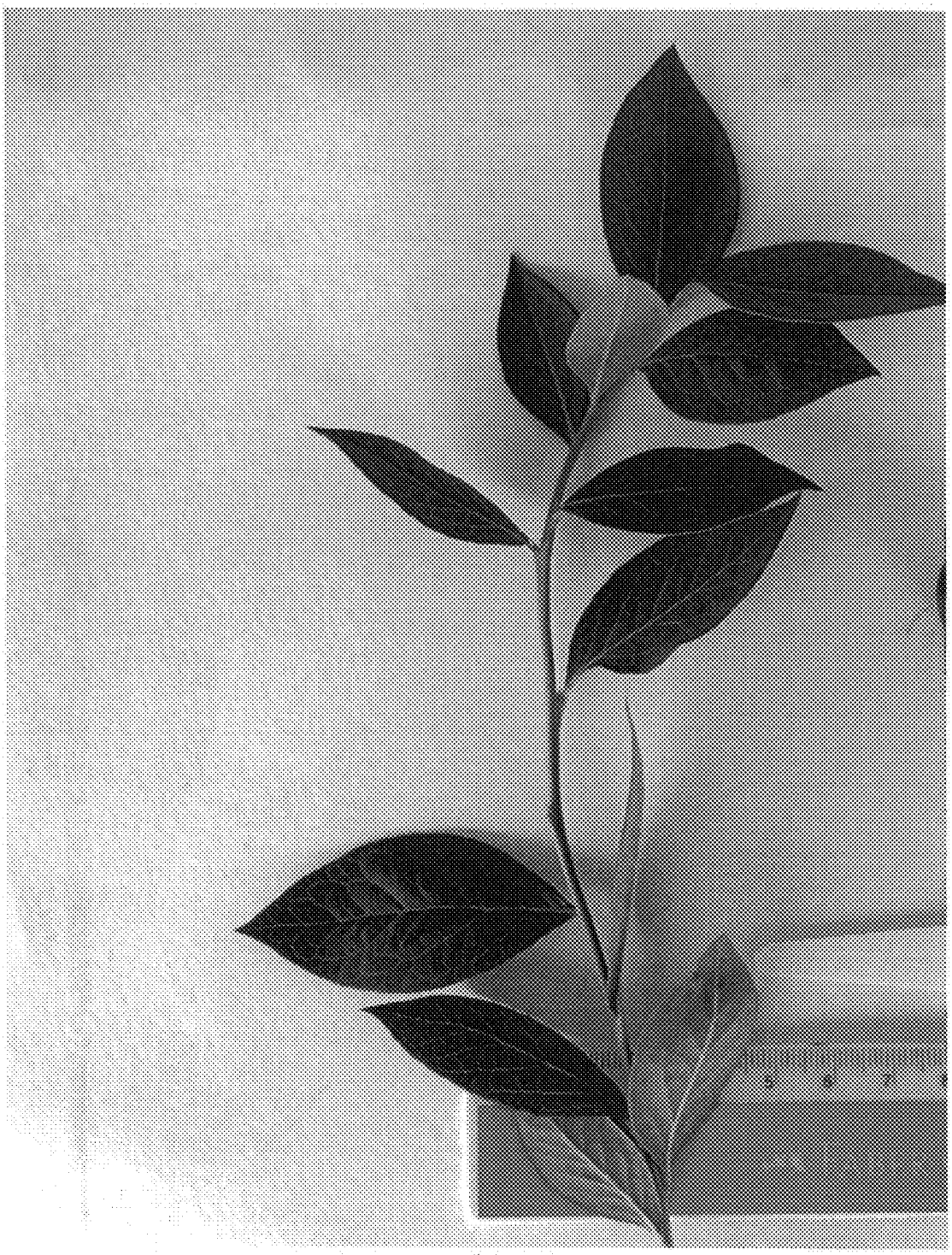
FIG. 2 depicts a twig bearing typical leaves and which shows the dorsal and ventral coloration thereof.

The colors in these photographs are as nearly true as is reasonably possible in a color representation of this type. Due to chemical development, processing and printing, the leaves and fruit depicted in these photographs may or may not be accurate when compared to the actual specimen. For this reason, future color references should be made to the common color description as provided hereinafter.

NOT A COMMERCIAL WARRANTY

The following detailed description has been prepared to solely comply with the provisions of 35 U.S.C. §112, and does not constitute a commercial warranty (either express or implied) that the present variety will, in the future, display the botanical, horticultural, or other characteristics as set forth, hereinafter. Therefore, this disclosure may not be relied upon to support any future legal claims including, but not limited to, breach of warranty of merchantability, or fitness for any particular purpose, or non-infringement, which is directed, in whole, or in part, to the present new variety.

DETAILED DESCRIPTION

Referring more specifically to the botanical details of this new and distinct variety of blueberry plant, the following has been observed during the sixth fruiting season under the ecological conditions prevailing at the farm of the inventor, which is located in Yanchep Springs, Yanchep Western Australia.

PLANT

Plant vigor: Strong to very strong. This is in contrast to the closest known variety, that being the 'Sharpeblue' blueberry plant (unpatented) and which is the closest known variety and which has a plant vigor characteristic which is considered only average to strong in comparison to other similar varieties.

Plant growth habit:

*Generally*.—Considered upright. This is in contrast to the growth habit which is expressed by the closest known variety and which is considered to be average.

Average plant size: About 1.8 meters in height, and about 1.5 meters in width.

Color:

*One year old shoots*.—Considered yellow-green (RHS 144A). This color is not distinctive of the present variety and is similar to the color as expressed by the closest known variety 'Sharpeblue'.

Internode length:

*One year old shoots*.—Considered medium for the species. This characteristic is distinguishable from the same growth characteristic as expressed by the closest known variety and which is medium to long.

LEAF

Leaf length: Considered average for the species, about 57 mm. This is in contrast to the closest known variety which has a leaf length which is considered average to long.

Leaf width: Considered average, about 32 mm. This is in contrast to the growth characteristic as expressed by the closest known variety where the leaf width is considered average to broad.

Leaf length/width ratio: Considered average. This is in contrast to the closest known variety where the same characteristic is considered average to large.

Leaf shape:

*Generally*.—Ovate. This is similar to the same growth characteristic as expressed by the 'Sharpeblue' blueberry plant.

Leaf color:

*Dorsal surface*.—Green (RHS 139A). This is similar to the growth characteristic as expressed by the closest known variety.

Leaf color:

*Ventral surface*.—Green. (RHS 138A).

Leaf color intensity:

*Dorsal surface*.—The present variety has a medium to dark green color. This is in contrast to the same growth characteristic as expressed by the closest known variety where the same green coloration is considered light to medium.

Leaf margin:

*Generally*.—Considered Entire. This is similar to the closest known variety.

FLOWER

Anthocyanin coloration: Considered very weak for the species. This is similar to the same growth characteristic as expressed by the closet known variety.

Inflorescence length: Considered average, about 10 mm. This is similar to the same growth characteristic as expressed by the closest known variety.

Average flower width about 8 mm.

Flower color: White. (RHS N155C).

Flower shape:

*Corolla*.—Urceolate.

Corolla tube:

*Size*.—Considered average. This is in contrast to the closest known variety where the size of the corolla tube is considered average to large.

Corolla tube coloration—anthocyanin: Very weak to weak. This is in contrast to the merely weak coloration of the corolla tube as seen in the closest known variety.

Corolla tube ridges: Present. These ridges are also seen in the closest known variety.

Average corolla lenght: About 8 mm.

FRUIT

Fruit cluster density: Considered dense. This is in contrast to the closest known variety where the same growth characteristic is seen as dense to very dense.

Unripe fruit:

*Color intensity*.—Considered average for the species yellow-green about (RHS 144B). This is in contrast to the growth characteristic as expressed in the closest known variety where the unripe fruit color is considered light to medium green.

Fruit size:

*Generally*.—Considered very large for the species, about 21 mm. This is in contrast to the fruit size as expressed by the closest known variety and where the fruit size is considered merely average. The fruit shape when viewed in a longitudinal section is considered oblate. This is similar to the closest known variety.

Sepal position: Considered semi-erect. This is in contrast to the sepal position or attitude characteristics as expressed by the closest known variety, that being, the 'Sharpeblue' blueberry plant and where the attitude of the sepals is considered to be merely erect.

Fruit sepal type: Considered incurving. This is in contrast to the same characteristic as expressed in the closest known variety and which is considered to be straight.

Calyx diameter basin: Considered average, about 9 mm. This is in contrast to the same characteristic expressed by the closest known variety and which is considered small to medium.

Calyx basin/depth: Considered average for the species, about 2 mm. This is very similar to the growth characteristic as expressed by the closest known variety.

Fruit:

*Bloom intensity*.—Considered strong. This is similar to what is seen in the closest known variety.

Skin color: Dark blue (RHS 203D). This color is similar to the color as seen in the closest known variety.

Fruit firmness: Generally speaking the present variety produces firm, to very firm fruit. This is in contrast to the soft to average firmness as typically experienced in the fruit produced by the closest known variety.

Fruit sweetness: Considered medium to high. This is in contrast to the closest known variety where the fruit sweetness is considered merely average.

Fruit acidity:

*Generally*.—Low to medium. This is in contrast to the closest known variety where fruit acidity is considered merely average.

Fruit flesh color: Yellow-green (RHS 145C).

Seed color: Grey-brown (RHS N199D).

Fruiting portions of the plant: Fruit may be found on one year old and current seasons shoots. This is similar to the same growth characteristics as expressed in the 'Sharpeblue' blueberry plant.

Time of vegetative bud burst: Generally speaking, the vegetative bud burst is considered to be very early in the season. This time of bud burst is earlier than that observed in the closest known variety.

Flowering time—one year old shoots: Considered very early in the season, and earlier in time than that as seen in the closest known variety.

Flowering time on current year's shoots: Considered very early in the season, and earlier in time than that as seen in the closest known variety.

Fruit ripening time on one year old shoots: Considered very early in the season for the species. This is in contrast to the same growth characteristic as expressed by the closest known variety 'Sharpeblue' blueberry plant, and where the time of fruit ripening begins early to medium in the season.

Fruit ripening time on current year's shoots: Considered very early in the season and earlier in time than the same growth characteristic as expressed by the closest known variety 'Sharpeblue' blueberry plant.

Resistance to insects and disease: No particular susceptibilities were noted. The present variety has not been tested to expose or detect any susceptibilities or resistances to any known plant and/or fruit diseases.

Although the new variety of blueberry plant possesses the described characteristics when grown under the ecological conditions prevailing near Yanchep Springs, Western Australia, it should be understood that the variations of the usual magnitude and characteristics incident to changes in growing conditions, fertilization, pruning, pest control, frost, climatic variables and horticultural management are to be expected.

Having thus described and illustrated my new variety of blueberry plant, what I claim is new and desire to secure by Plant Letters Patent is:

1. A distinct variety of blueberry plant, substantially as illustrated and described and which is characterized principally as to novelty by producing fruit which are mature for harvesting and shipment very early in the season, and which are further very large in size, and wherein further, the plant exhibits an upright growth pattern under the ecological conditions prevailing near Yanchep Springs, Western Australia.

* * * * *